United States Patent [19]

Tou et al.

[11] Patent Number: 4,944,180

[45] Date of Patent: Jul. 31, 1990

[54] PERMEATION MEASUREMENT DEVICE

[75] Inventors: James C. Tou; Donald C. Rulf, both of Midland, Mich.

[73] Assignee: The Dow Chemical Company, Midland, Mich.

[21] Appl. No.: 237,290

[22] Filed: Aug. 26, 1988

[51] Int. Cl.$^5$ .......................................... G01N 15/08
[52] U.S. Cl. ........................................................ 73/38
[58] Field of Search ................... 73/38, 40.7; 250/288, 250/289

[56] References Cited

U.S. PATENT DOCUMENTS

| | | | |
|---|---|---|---|
| 3,618,361 | 11/1971 | Stephens et al. | 73/38 |
| 4,464,927 | 8/1984 | Reid | 73/38 |
| 4,468,951 | 9/1984 | Garcia et al. | 73/38 |
| 4,506,542 | 3/1985 | Rose | 73/38 |
| 4,660,411 | 4/1987 | Reid | 73/38 |
| 4,791,292 | 12/1988 | Cooks et al. | 250/288 |

FOREIGN PATENT DOCUMENTS

| | | | |
|---|---|---|---|
| 2926112 | 1/1981 | Fed. Rep. of Germany | 73/40.7 |
| 190640 | 10/1984 | Japan | 73/38 |
| 794411 | 1/1981 | U.S.S.R. | 73/38 |
| 1045083 | 9/1983 | U.S.S.R. | 73/38 |
| 1192033 | 5/1970 | United Kingdom | 73/38 |

OTHER PUBLICATIONS

"Mass Spectrometric Studies of Diffusion and Permeability in Polymeric Films", by R. L. Bredeweg and V. J. Caldecourt. The Fourteenth Annual Conference on Mass Spectrometry and Allied Topics, Paper 29, Dallas, TX, May 22-27, 1966.
"Measurement of Odour Permeability of Polypropalene Packaging Films at Low Odourant Levels", by M. G. R. Zobel, Polm Testing, 3 (1982) 133.
"An Exceedingly Simple Mass Spectrometer Interface with Application to Reaction Monitoring an Environment Analysis", J. B. Brodbelt and R. G. Cooks, Anal. Chem. 57 (1985) 1153.
"Measurement of Hydrogen Isotope Transport in Poly (vinyl fluoride) Films by the Permeation-Rate-Method", by K. D. Ziegel, H. K. Frensdorff and D. E. Blair, J. Polym Sci., Part A-2 7 (1969) 809.
"A Dynamic Approach to Diffusion and Permeation Measurements", by R. A. Pasternak, J. F. Schimscheimer and J. Heller, J. Polymer Sci. Part A-2, 8 (1970) 467.
"Atmospheric-Pressure Ionization Mass Spectrometric and Photoionization Techniques for Evaluation of Barrier Film Permeation Properties", by V. J. Caldecourt and J. C. Tou, J. Membrane Science, 29 (1986).
"High Barrier Packaging and Flavor Aroma and Packaging", Laminations and Coatings Conference, Book 2, 337–339 and pp. 411–450, Chicago, IL, Sep. 9–11, 1985.
"Flavor and Odor Considerations With New Types of Food Packages: An Overview", S. Abbe, B. M. Bassett, and J. C. Bassett, and J. C. Collier, Lamination & Coatings Conference, Book, 2, 411–450, Chicago, IL, Sep. 9–11, 1985.

(List continued on next page.)

*Primary Examiner*—Hezron E. Williams
*Assistant Examiner*—Joseph W. Roskos
*Attorney, Agent, or Firm*—Harness, Dickey & Pierce

[57] ABSTRACT

A system for measuring the permeation rate of organic molecules across a polymer film, which includes a membrane chamber, an electron impact mass spectrometer and a flow-through hollow fiber probe for providing an interface between the membrane chamber and the mass spectrometer. The membrane chamber supports the polymer film sample to be tested, and permits one side of the sample to be exposed to a vapor containing a known concentration of organic molecules under substantially atmospheric pressure and controlled environmental conditions on both the upstream and downstream sides of the sample. The membrane chamber features a unique permeation cell and sample holder arrangement which employs a pair of adhesive backed cards to sandwich the sample and maintain a permanent desirable alignment of the sample.

16 Claims, 7 Drawing Sheets

OTHER PUBLICATIONS

"The Odour Permeability of Polypropylene Packaging Film", M. Zobel, Polymer Testing 5 (1985) 153–165.

"Membrane Interface for Selective Introduction of Volatile Compounds Directly into the Ionization Chamber of a Mass Spectrometer", M. Bier and R. Cooks, Anal. Chem. 1987, 59, 597–601.

"Novel Mass Spectrometric Sampling Device–Hollow Fiber Probe", L. B. Westover, J. C. Tou and J. H. Mark, Analytical Chemistry, vol. 46. p. 568. Apr. 1974.

"The Construction and Use of Simple Interfaces for Combined Liquid Chromatography Mass Spectrometry", N. Evans and J. Williamson, Biomedical Mass Spectrometry, vol. 8, No. 7, 1981, pp. 316–321.

"Transport of Apple Aromas in Polymer Films", P. T. Delassus, J. C. Tou, M. A. Babinec, D. C. Rulf, B. K. Karp, and B. A. Howell, ACS Symposium No. 365, Food and Packaging Interactions, Chapter 2, pp 11–27, Ed. Joseph H. Hotchkiss, 1988.

PERMEATION MEASUREMENT DEVICE

BACKGROUND AND SUMMARY OF THE INVENTION

Polymeric materials have become increasingly important in the food packaging industry because of their lighter weight, lower cost, and easier processing as compared to the conventional materials such as glass, steel, and aluminum. The barrier properties of the polymeric materials against the food flavor and aroma constituents at different conditions are critical to the suitability of such applications. Generally speaking, there are two major channels available for the losses of the flavor and aroma components to the packaging materials. One is the transmission loss due to the permeation of the flavor/aroma molecules across the polymeric films to the environment, and the other is the sorption loss due to the solubility of the flavor and aroma molecules in the polymer. The permeation rate or permeability at normalized conditions depend on both solubility and diffusivity of the molecules of the polymeric films. Both of the losses have an impact on the shelf life of the packaged food.

Since useful packaging materials must exhibit very low solubility and diffusivity, the measuring techniques must have high sensitivity. In this regard, several techniques have been reported in the literature. For example, an electron impact mass spectrometric technique with high sensitivity and specificity for the permeation rate measurements was reported in "Mass Spectrometric Studies of Diffusion and Permeability in Polymer Films", by R. L. Bredeweg and V. J. Caldecourt, The Fourteenth Annual Conference on Mass Spectrometry and Allied Topics, Paper 29, Dallas, Tex., May 22–27, 1966. However, this technique requires that the permeating side of a membrane be exposed to high vacuum for mass spectrometric analysis. This requirement may alter the permeation characteristics of a membrane due to possible physical changes resulting from the vacuum seal and support.

An apparatus based upon flame ionization techniques was discussed in "Measurement of Odor Permeability of Polypropylene Packaging Films at Low Odorant Levels", by M. G. R. Zobel, Polm. Testing, 3 (1982) 133. There it was reported that measurements of permeation rates were capable of being made down to about $3 \times 10^{-12}$ Kg·m$^{-2}$·sec$^{-1}$. However, because of the nature of flame ionization, the technique is incapable of measuring the permeation rates of mixtures.

Two additional techniques based upon atmospheric pressure ionization mass spectrometry and photoionization were discussed in "Atmospheric-Pressure Ionization Mass Spectrometric and Photoionization Techniques for Evaluation of Barrier Film Permeation Properties", by V. Caldecourt and J. C. Tou, J. Memb. Sci., 29 (1986). While these techniques provided comparable sensitivity to that of the flame ionization technique identified above, the photoionization technique did present another drawback. Specifically, the photoionization detector tends to be coated by the photodecomposition products from the permeating molecules resulting in a sensitivity decrease. Additionally, the atmospheric pressure ionization mass spectrometric technique suffers from its inherent narrow dynamic range. Moreover, judgment and further validation would occasionally complicate the operation.

Therefore, the need still exists for a general and reliable technique for the evaluation of the flavor/aroma permeation across a polymer film with its back side at ambient pressure.

Accordingly, it is a principal objective of the present invention to provide a mass spectrometric based system for measuring aroma/flavor permeation rates across polymer films which will be highly sensitive and reliable.

More specifically, it is an objective of the present invention to provide a mass spectrometric based system which is capable of determining permeability, diffusivity and solubility of aroma/flavor constituents of polymeric films with both the feed side and the permeating side of the film at or about ambient pressure.

It is an additional objective of the present invention to provide a permeation measurement device which is capable of achieving parts per billion sensitivity to organic molecule containing vapors with feed concentrations down to the parts per million level.

It is another objective of the present invention to provide a permeation measurement device which is capable of determining the diffusivity and solubility of films where these coefficients cannot be adequately determined from the fast rising transient portion of the permeation curve.

It is a further objective of the present invention to provide a permeation cell and film holder arrangement which enables a film sample to be removed and reinserted into the cell as often as desired with exactly the same alignment.

It is yet an additional objective of the present invention to provide a permeation cell with a film holder which prevents stresses. irregularities or fingerprints from being introduced into the film sample.

It is yet another objective of the present invention to provide a permeation measurement device which permits the exposure of polymer films to gaseous mixtures containing known concentrations of organic molecules under controlled temperature, pressure, and humidity conditions.

It is still another objective of the present invention to provide a permeation measurement device which is capable of independently controlling vapor composition and humidity on each side of the polymer film sample.

To achieve the foregoing objectives, the present invention generally comprises a system for measuring the permeation rate of organic molecules across a polymer film, which includes a membrane chamber, an electron impact mass spectrometer and a flow-through hollow fiber probe for providing an interface between the membrane chamber and the mass spectrometer. The membrane chamber supports the polymer film sample to be tested, and permits the sample to be exposed to a vaporous fluid containing a known concentration of organic molecules under substantially atmospheric pressure and controlled environmental conditions on both the upstream and downstream sides of the sample.

The membrane chamber features a unique permeation cell and sample holder arrangement which substantially enhances the operation of the permeation rate measurements. Specifically, the polymer film sample is held between a pair of adhesive backed cards for maintaining a permanent desirable alignment of the sample, as well as permitting convenient placement of the sample into the permeation cell and later storage of the sample. The permeation cell includes a pair of metal disks between which the sample holder assembly is positioned, and fluid pressure operated cylinders for moving the disks into and out of a sealing engagement with the sample. One of the metal disks is formed to provide an upstream cavity, while the other metal disk is formed to provide a downstream cavity. Each of the metal disks is also provided with a pair of ports, so that separate fluids may be swept across each side of the sample.

Additional advantages and features of the present invention will become apparent from a reading of the detailed description of the preferred embodiments which makes reference to the following set of drawings in which:

BRIEF DESCRIPTION OF THE DRAWINGS

FIGS. 5 and 6 are elevation views of the disks shown in FIG. 4 for supporting the polymer film sample holder assembly in the permeation cell shown in FIG. 4.

Specifically.

DETAILED DESCRIPTION OF THE PREFERRED EMBODIMENT

Figure 1:
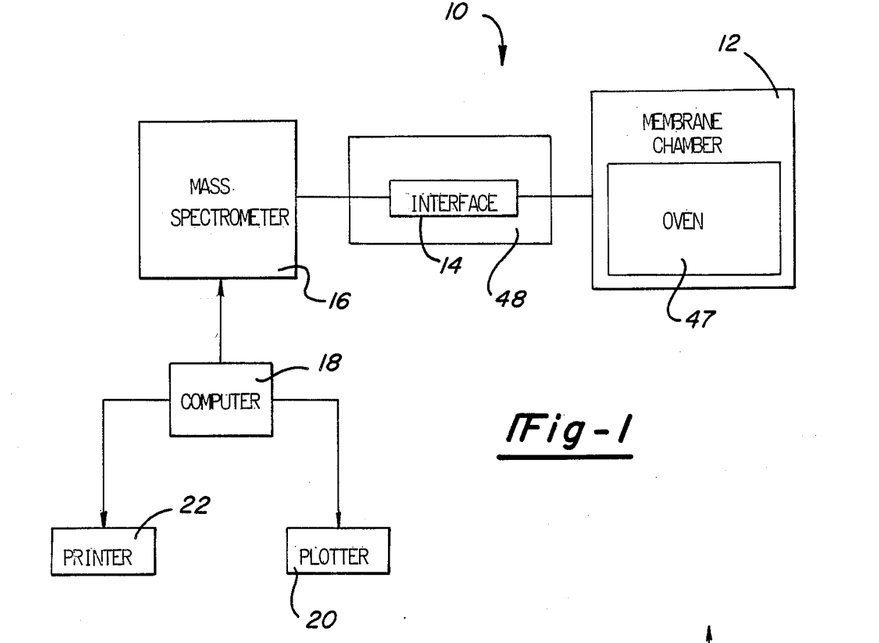
FIG. 1 is a block diagram of the permeation measurement system according to the present invention.

Referring to FIG. 1, a block diagram of a permeation measurement system 10 according to the present invention is shown. The permeation measurement system 10 generally comprises a membrane chamber 12, an interface device 14 and a mass spectrometer 16. The membrane chamber 12 is adapted to support the polymer film sample to be tested, and permit the sample to be exposed on one side to a gaseous or vaporous fluid containing a known concentration of organic molecules. The membrane chamber 12 and its unique sample holding arrangement will be more fully discussed in connection with FIGS. 3–8.

The interface 14 is connected between the output of the membrane chamber 12 and the input of the mass spectrometer 16. The interface 14 enables organic molecules which have permeated across the polymer film sample (at substantially atmospheric pressure) to be introduced into a mass spectrometer which operates under high vacuum conditions. In this regard, the mass spectrometer 16 is an electron impact mass spectrometer, and the interface is constructed to introduce the permeant organic molecules directly into the ion source of the mass spectrometer 16. Electron impact mass spectrometers are known for their wide dynamic range, broad range of applications to a variety of chemicals, and ready commerical availability. Thus, the interface 14 makes it possible to use such a high vacuum mass spectrometer, while permitting the polymer sample film to be tested under substantially ambient pressure conditions.

FIG. 1 also shows that the mass spectrometer 16 is equipped with a computer 18, a plotter 20 and a printer 22. In this system configuration, the mass spectrometer 16 operates in conjunction with the computer 18 for analyzing the concentration of organic molecules sensed by the mass spectrometer's detector. The results of this analysis may then be displayed in graphical form on the plotter 20 or in numeric form on the printer 22. In one embodiment of the present invention, the mass spectrometer 16 is a Hewlett-Packard 5970B Mass Selective Detector, the computer 18 is a Hewlett-Packard 59970C monochromatic workstation, the plotter 20 is a Hewlett-Packard 7475A six pen plotter, and the printer 22 is a Hewlett-Packard 2225A Think Jet printer. However, it should be appreciated that other suitable mass spectrometers may be used in the appropriate application.

Figure 2:
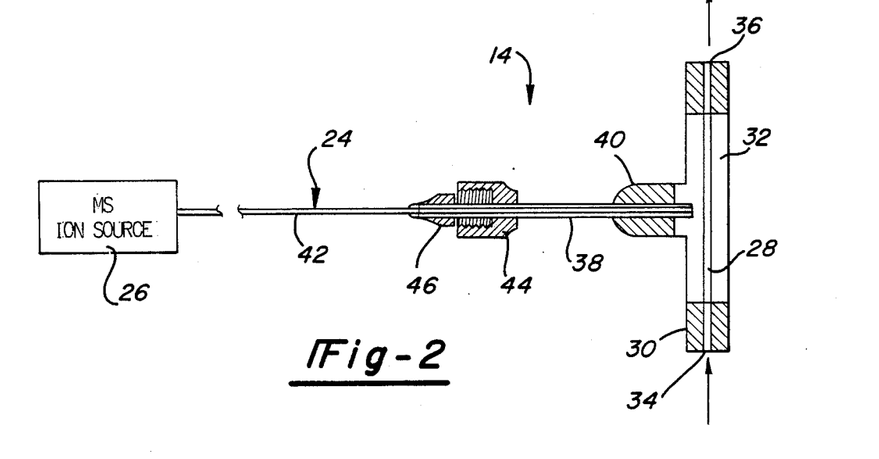
FIG. 2 is a cross-sectional view of the interface shown in FIG. 1.

Referring to FIG. 2, a cross-sectional view of the preferred construction for the interface 14 is shown. In this regard, it has been found that the construction of the system's interface may have a significant effect on the sensitivity of the analysis. Specifically, with the interface construction of FIG. 2, it is possible to achieve parts-per-billion sensitivity for monitoring volatile organics in air or nitrogen. The interface 14 of FIG. 2 is generally comprised of a flow-through hollow fiber probe 24, which has one end inserted into the ion source 26 of the mass spectrometer 16. This interface construction is referred to as a flow-through hollow fiber probe, because it is based upon the principal of flowing an analyte through a semipermeable hollow fiber.

The probe 24 includes a semipermeable hollow fiber 28 which is mounted into a tee 30. Specifically, the hollow fiber 28 extends coaxially through an elongated cylindrical bore 32 of the tee 30, such that fluid may flow through the interior of the hollow fiber via ports 34 and 36 at opposite ends of the tee. The probe 24 also includes a tube 38 which is extends into a side arm 40 of the tee 30, and a column 42 which extends coaxially through the tube 38. Finally, the probe 24 includes fitting members 44 and 46, which are used to connect the probe 24 to the mass spectrometer 16.

In one form of the present invention, the hollow fiber ZS Ia a Dow Corning Silastic medical grade tubing (0.020" ID ×0.037" OD), and the tee 30 is made from glass or stainless steel (2"×¼"). Additionally, the tube 38 is made from stainless steel (1/16"), the column 42 is made from uncoated fused silica (16" 50 micron), and the fitting members 44–46 are Swagelok fittings using Vespel ferrules. The seal between the hollow fiber 28 and the tee 30, and the seal between the tube 38, column 42 and the tee 30 are achieved using Torr Seal (Varian Associates, Vacuum Division, Palo Alto, Calif.).

While other suitable interface constructions may be used in the system 10, use of the probe 24 is preferred due to the sensitivity that can be reached with this construction. Another construction which could be used for the interface 14 is described in "An Exceedingly Simple Mass Spectrometer Interface with Application to Reaction Monitoring and Environment Analysis", J. B. Brodbelt and R. G. Cooks, Anal. Chem. 57 (1985) 1153. This article describes a flow-through hollow fiber probe which was demonstrated to be useful for reaction monitoring and environmental analysis of volatile organics in aqueous and organic solutions. This article is hereby incorporated by reference.

The probe 24 is preferably housed in a thermostatic enclosure located between the mass spectrometer entrance point and the side wall of an oven which contains the permeation cell according to the present invention. The oven is shown in block form in FIG. 1, and is generally designated by the reference numeral 47. Similarly, the enclosure for the interface is designated by reference numeral 48 in FIG. 1. While the oven 47 controls the temperature to which the polymer film membrane is subjected, the thermostatic enclosure 48 independently controls the temperature of the interface 14. In this regard, it has been found that the response time of the flow-through hollow fiber type of interface is dependent on temperature. Specifically, at elevated temperatures, the response time is shorter. For example, at seventy five degrees (C), the response time was observed to be approximately one minute. Temperature stability of the ion source 26 may also have an affect on the permeation measurements. Accordingly, it is preferred that the filament of the ion source heater be left on for one hour before permeation measurements are started.

Figure 3:
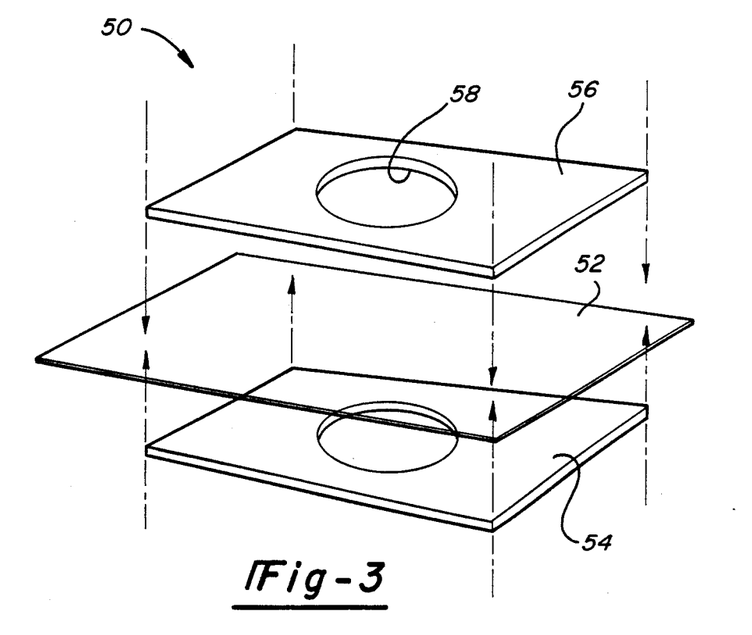
FIG. 3 is an exploded view of a sample holder assembly used to maintain the polymer film sample in a predetermined position.

Referring to FIG. 3, an exploded view of a sample holder assembly 50 according to the present invention is shown. The sample holder assembly 50 generally comprised of a polymer film 52 which is sandwiched between two identical cards 54–56. Each of the cards 54–56 has a central aperture 58, so that a predetermined portion of both sides of the film sample 52 will be exposed. In a preferred form of the invention, each of the cards 54–56 is made from die-cut paper card stock, and each card has an adhesive layer on one side thereof. The side of the cards with the adhesive layer faces the film sample in order to secure the film sample in a desired permanent position between the two cards.

It should be appreciated from the above that this sample holder arrangement enables the film sample 52 to be rigidly held in a generally flat position without any stresses, wrinkles, creases or other irregularities. Additionally, this arrangement enables the film sample 52 to be handled without touching the film itself, so that the film will not be contaminated with fingerprints. Furthermore, notations can be written on one or both of the cards, and the assembly can be conveniently stored for future reference. The low cost of this assembly also permits it to be disposable if desired.

It should also be appreciated that it may be desirable to mount the film sample 52 to only one of the cards 54–56. Similarly, other suitable materials besides paper card stock may be used for the cards 54–56. As will be seen more fully in connection with FIG. 4, this assembly permits the film sample to be easily inserted into and removed from the permeation cell, not just once, but repeatedly with the same alignment.

Figure 4:
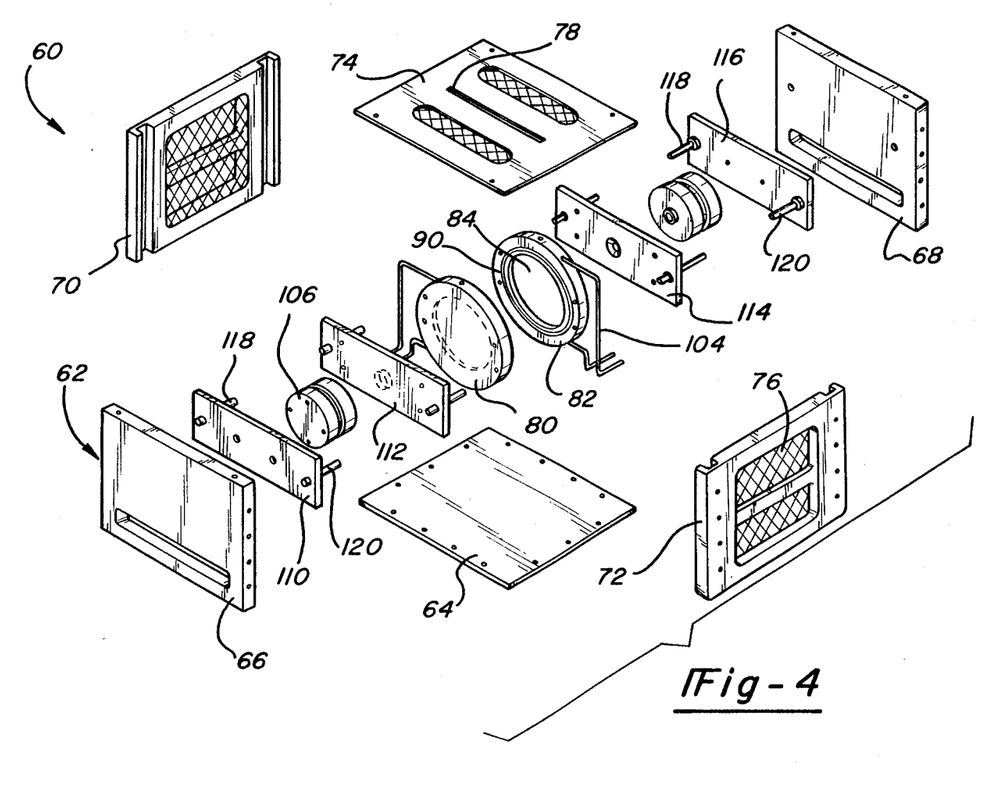
FIG. 4 is an exploded assembly view of a permeation cell which is contained in the membrane chamber shown in FIG. 1.

Referring to FIG. 4, an exploded view of a permeation cell 60 according to the present invention is shown. The permeation cell 60 includes a housing 62, which is generally comprised of a base plate 64, a pair of opposing end plates 66–68 mounted to the base plate, a pair of opposing side plates 70–72 mounted to both the end plates and the base plate, and a top plate 74 mounted to the end and side plates. Accordingly, it should be appreciated that the housing 62 has a box-like configuration, which may be made of fabricated steel. Due to the fact that the permeation cell 60 is constructed to avoid any need to open the housing 62, a number of apertures are provided in the housing structure, such as aperture 76, so that the operation of the permeation cell may be viewed from the outside.

The top plate 74 of the housing 60 includes an elongated slot 78 which is adapted to receive the sample holder assembly 50 of FIG. 3. Once the assembly 50 is inserted into the housing 60 through slot 78, the assembly will be supported between a pair of movable steel disks 80–82. As may be best seen in FIGS. 5 and 6, each of the disks 80–82 are machined to provide a generally circular cavity, so that when the assembly 50 is clamped between the disks, a permeation chamber is formed by these cavities. In this regard, the polymer film sample 52 separates the cavities of the permeation chamber into an upstream side and a downstream side.

Figures 5A, 5B:
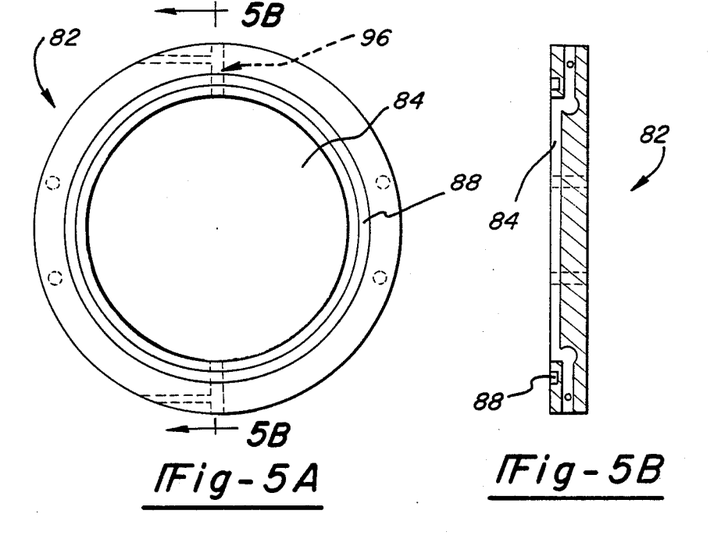
FIG. 5A is an elevational plan view of a disk shown in FIG. 4.
FIG. 5B is an elevational side view of the disk of FIG. 5A.
Figure 6A:
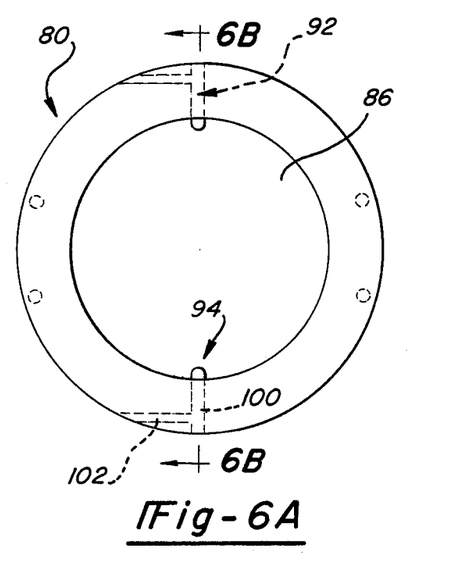
FIG. 6A is an elevational plan view of a disk shown in FIG. 4.
Figure 6B:
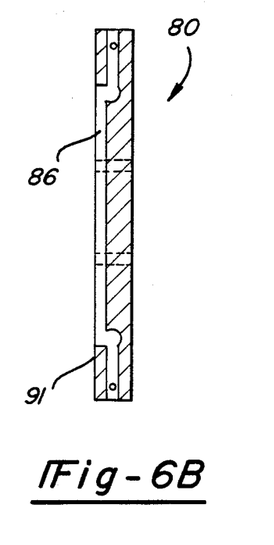
FIG. 6B is an elevational side view of the disk of FIG. 6A.

FIGS. 5A and 5B show two views of the "downstream" disk 82, while FIG. 6A and 6B show two corresponding views of the "upstream" disk 80. In FIGS. 5A and 5B, the cavity of the downstream disk 82 is identified by reference numeral 84. Similarly, in FIGS. 6A and 6B, the cavity of the upstream disk 80 is identified by reference numeral 86. The downstream disk 82 also includes an annular groove 88, which is used to seat a Viton O-ring 90. The diameter of this elastomeric O-ring is smaller than the aperture 58 in the cards 54–56, so that the O-ring will engage one side of the film 52 and press the other side of the film against the smooth surface 91 of the upstream disk 80 as the disks are clamped together. Accordingly, the O-ring 90 serves to seal the upstream and downstream cavities of the permeation chamber, and the wide, smooth surface 91 of the upstream cavity 86 permits some lateral misalignment to occur without adversely affecting this seal.

In order to sweep a gaseous vapor containing organic molecules across the upstream cavity 86 of the permeation chamber, the disk 80 includes a pair of diametrically opposing ports 92–94. One of the ports 92–94 enables the vapor to enter the upstream cavity 86, while the other port permits the vapor to escape the cavity. The downstream disk 82 is also formed with a pair of ports 96–98 for permitting a carrier gas to sweep across the downstream cavity 84. Each of these ports includes a radial passageway 100 which extends into its respective cavity, and a lateral passageway 102 which connects the radial passageway to the exterior of the disk.

As shown is FIG. 4, a stainless steel tube 104 is connected to each of the lateral passageways 102, in order to transmit the carrier gas and feed vapor both to and from the permeation cell 60. Even though the disks 80 and 82 are mounted for axial movement within the permeation cell 60 (e.g., ½ inch), the tubes 104 are suitably angled, as shown, to enable these tubes to bend with this movement. In accordance with the present invention, the disks 80 and 82 are mounted such that the operator does not have to touch these disks in order to open and close the permeation chamber. Since it may be desirable to conduct permeation experiments at elevated temperatures, this mounting arrangement enhances the safety of the procedure. Similarly, there is no need to cool and reheat the permeation cell, as would otherwise be the case.

In this regard, the permeation cell 60 includes a pair of pneumatically operated cylinders 106 and 108 for opening and closing the permeation chamber. These cylinders not only enable the clamping force to be controlled by air pressure (e.g., 100–200 psi) uniformly applied around the disks, but they also permit the permeation chamber to be rapidly opened and closed. The cylinder 106 is mounted between a pair of guide plates 110.112. Similarly, the cylinder 108 is mounted between a pair of guide plates 114–116. These guide plates are movably supported by a pair of opposing guide rods 118–120, which are connected to the end plates 66–68. The disk 80 is mounted to the guide plate 116, while the disk 82 is mounted to the guide plate 114.

While this particular embodiment employs two fluid controlled cylinders 106–108 for opening and closing the permeation chamber, it should be appreciated that it may be possible to employ only one such cylinder in the appropriate application. It should also be appreciated that the disks 80–82 need not have an annular shape, and that other suitably inert and rigid materials may be used to construct the permeation cell 60 other than steel.

Figure 7:
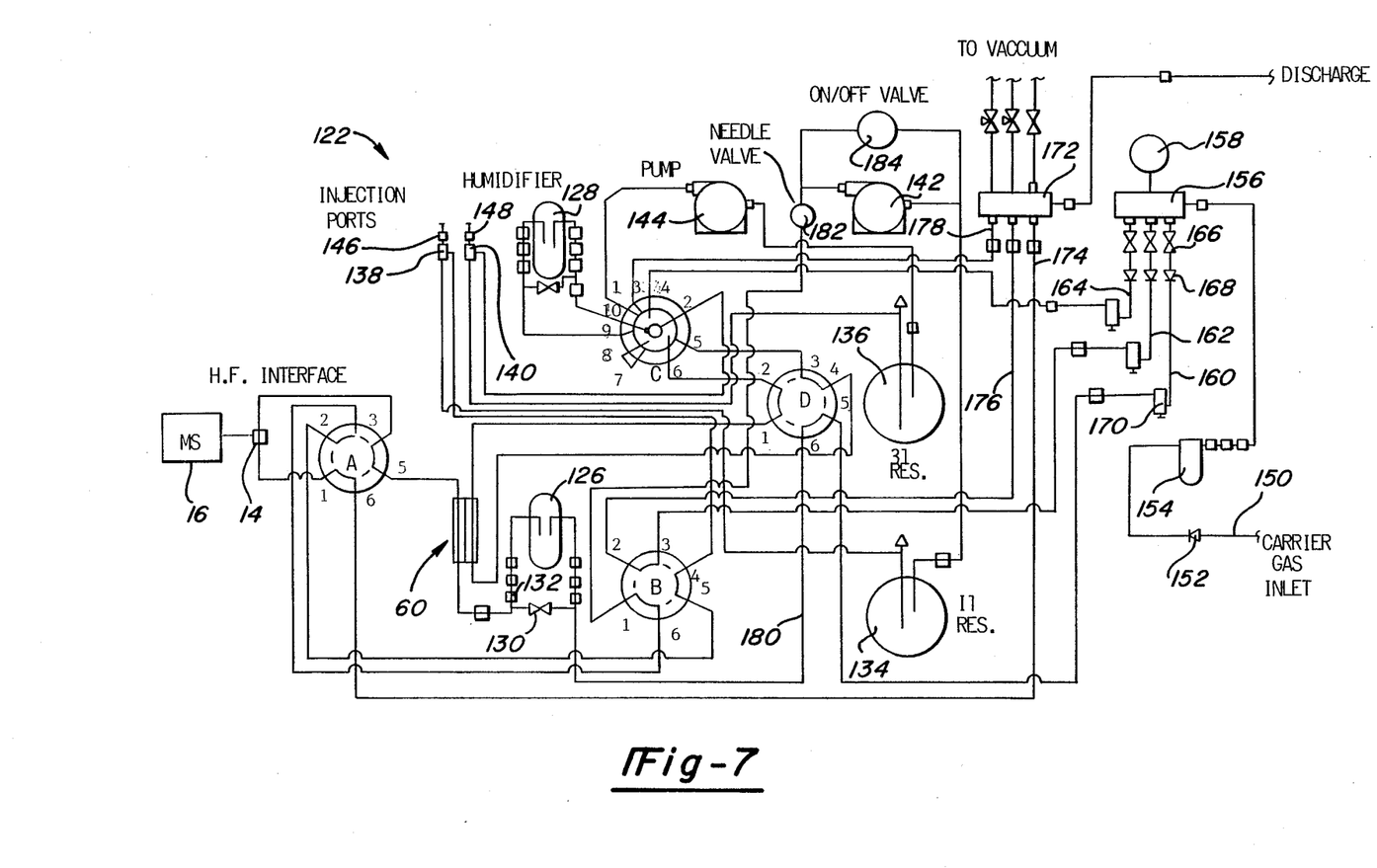
FIG. 7 is a diagrammatic view of a fluid handling apparatus which forms part of the membrane chamber shown in FIG. 1.

Referring to FIG. 7, a schematic diagram of the fluid handling apparatus 122 apparatus according to the present invention is shown. This fluid handing apparatus, along with the temperature control apparatus 124 of FIG. 8 combine to simulate real-world conditions for testing the permeability of the film sample 52. In this regard, most of this equipment is contained in the oven 47 to provide temperature control both above and below the ambient temperature. In this particular embodiment, the various valves, flow meters and humidity control equipment of FIG. 7 are preferably mounted to an aluminum framework outside of the oven 47, and the cover of the oven is preferably hinged at the top to provide ready access to the slot 78 of the permeation cell 60.

The fluid handling apparatus 122 of FIG. 7 includes a multi-port valve A connected between the exit port of the downstream side of the permeation cell 60 and the interface 14, and a humidity control device 126 connected between the entrance port of the downstream side of the permeation cell and a multi-port valve B. Another humidity control device 128 is connected to a multi-port valve C for controlling the humidity in the upstream side of the permeation cell 60. Each of these humidity control devices generally comprise a fabricated glass bubbler mounted in a separate, independently controlled thermostat, and the bubbler preferably contains a saturated salt solution. Each of the humidity control devices 126–128 also includes a bypass valve 130. It should also be noted that the small blocks located throughout FIG. 7, such as block 132, simply represent fittings used to connect the stainless steel tubes used to interconnect the various fluid handling components in the system.

The fluid handling apparatus 122 also includes a pair of reservoirs 134 and 136. The reservoir 134 is used to contain a supply of a calibration mixture, while the larger reservoir 136 is used to contain a supply of a feed mixture. For permeation measurements, the calibration mixture is a vapor containing a small, known amount of the organic molecules used to test the film sample 52 in a carrier gas which is inert to the chemistry of the test. This calibration mixture is used to calibrate the sensitivity of the mass spectrometer 16. The feed mixture is also a vapor which contains a larger, known amount the the organic constituents of the calibration mixture in an inert carrier gas.

A pair of injection ports 138 and 140 provide a means for introducing the organic constituents of a compound or mixture into the reservoirs 134 and 136, respectfully. In this regard, a pair of pumps 142 and 144 (Model MB-21, Metal Bellows Corp., Sharon, Mass.) are used to circulate the carrier gas through their respective reservoirs and past their respective injection ports in separate recirculation loops which permit the organic constituents to be injected into these loops via syringes 146 and 148. The carrier gas (e.g., nitrogen) is introduced into the fluid handling apparatus 122 via tube 150. The carrier gas is transmitted through a check valve 152, a filter 154 and a manifold 156. A pressure gauge 158 is connected to the manifold 156, and the manifold provides three separate supply lines 160–164. Each of these supply lines includes a valve 166, a check valve 168 and a flow meter 170.

The fluid handling apparatus 122 also includes a manifold 172 which connects three discharge lines 174.178 to either a vacuum source or a discharge gas hood. The apparatus 122 also includes a valve D which operates in combination with valve C and the pump 144 to convey the feed vapor mixture from the reservoir 136 to the upstream side of the permeation cell 60. The valve D also permits the upstream side of the permeation cell 60 to be purged with carrier gas via lines 160 and 180. The calibration supply system also includes a needle valve 182 and a bypass valve 184 connected to the pump 142 to control the flow of the calibration mixture through the hollow fiber probe 24 of the interface 14. In this regard, it should be appreciated that this flow rate should be considerably slower than that used for filling the reservoir 134.

Figure 8:
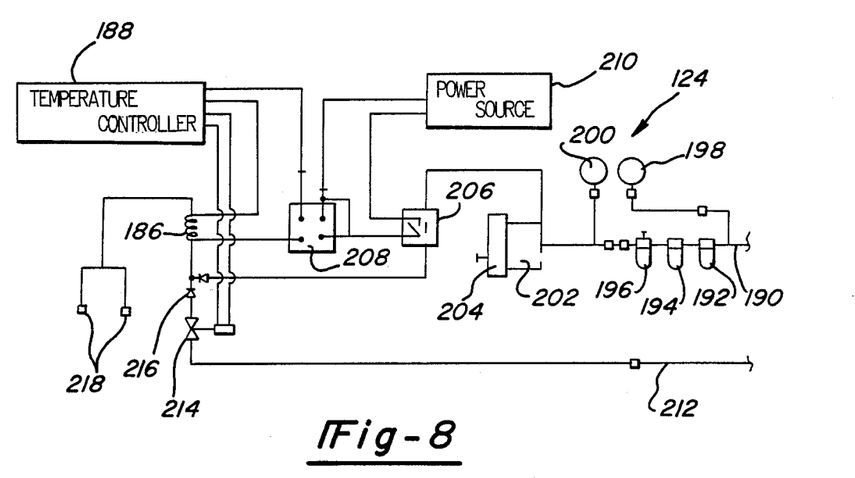
FIG. 8 is a diagrammatic view of the temperature control apparatus used in the membrane chamber shown in FIG. 1.

Referring to FIG. 8, a schematic diagram of the temperature control apparatus 124 according to the present invention is shown. The temperature control apparatus 124 includes a heating element 186 for the air convection oven 47, which operates under the control of a duel set point temperature controller 188. In this regard, air (or other suitable gas) is introduced into the system via line 190. The line 190 includes a pair of filters 192–194 and a filter/regulator 196 interposed between a pair of pressure gauges 198–200. A pressure regulator 202, a flow meter 204 and an air flow switch 206 are also included in the line 190. The air flow switch 206 operates in conjunction with a relay 208 (under power supplied by DC power source 210), to turn on the heating element only when air flow is present.

The temperature control apparatus 124 also includes another supply line 212 for providing a cooling fluid, such as $CO_2$. In this regard, a solenoid valve 214 is operates under the control of the temperature controller 188 to permit fluid flow from the line 212 through the check valve 216 and the oven 47, and out through the oven ports 218. Thus, it should be appreciated that the temperature control apparatus 124 permits the temperature to be controlled both above and below ambient conditions.

With respect to the method of operation, the vapor calibration standard is first prepared by injecting a defined amount of a $CH_2CL_2$ (or other solvent) solution of a compound or a mixture of interest into the injection port 138 while the pump 142 is recirculating the carrier gas past this injection port. Calibration of the mass spectrometer's sensitivity is then performed with the calibration standard from the reservoir 134 via pump 142 and valve B. The feed vapor is then prepared by injecting a defined amount of the compound or mixture into the injection port 140 while the pump 144 is recirculating the carrier gas past this injection port.

The permeation experiment is then performed by causing the feed vapor to circulate through the upstream side of the permeation cell 60 (via pump 144, valve G, humidifier 128 and valve D), while carrier gas from line 150 is swept through the downstream side of the permeation cell and into the interface 14 (via pump 142, valve B and humidifier 126). As stated previously, this experiment may be conducted at or near ambient pressure to simulate real-world operating conditions.

After the permeation experiment is completed, then a desorption experiment is preferably conducted according to the method of the present invention. This method was developed to study the actual amount of permeating molecules in the film sample 52 after the steady state condition has been reached in the permeation experiment. This desorption experiment is useful in studying films that exhibit very high diffusivity, such as polyethylene based films. In such cases, the instrumental response time may be too slow to follow the permeation rate change during the transient period.

A prerequisite for the desorption experiment is to ensure the absence of residual permeating molecules in the upstream side of the system. Accordingly, it is preferred that the pump 142 is turned off, and vacuum is applied to the upstream side of the system to rapidly flush this side of the system with carrier gas. Then, the vacuum is switched off, and the flow of carrier gas is restored through the upstream side of the system. Using this procedure, it takes only about five minutes before measurement of the desorption of permeant molecules through the film sample 52 may be made from the downstream side of the system.

Figure 9A:
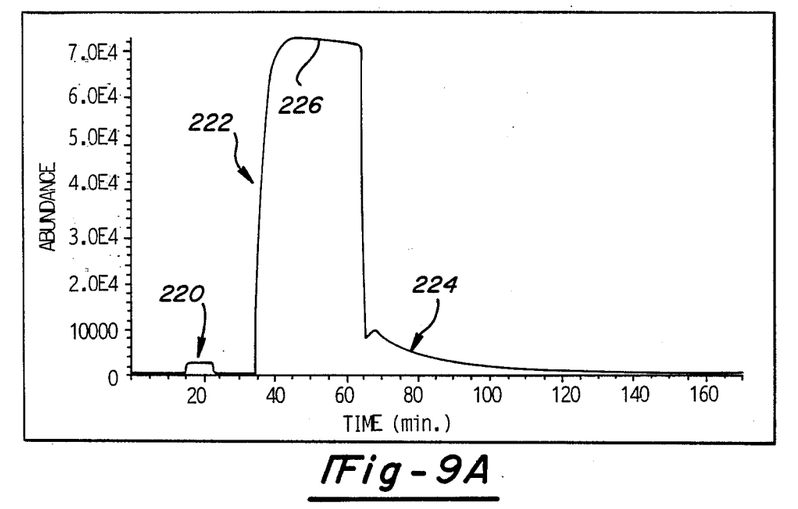
FIG. 9A is a graph of a permeation measurement utilizing the system shown in FIG. 1.
Figure 9B:
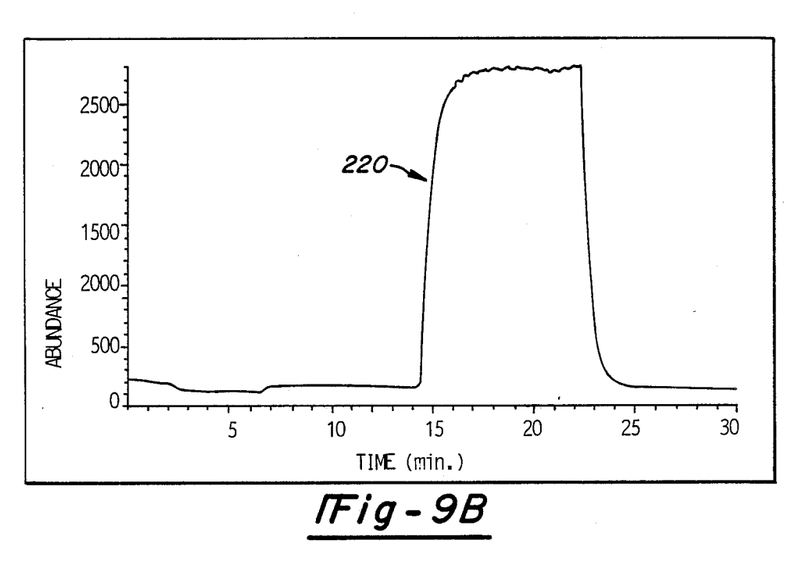
FIG. 9B is an expanded graph of the calibration section from the graph shown in FIG. 9A.

This experimental procedure is shown graphically in FIGS. 9A–9D. FIG. 9A represents a composite graph of the calibration curve 220 of FIG. 9B, the permeation rate curve 222 of FIG. 9C, and the desorption curve 224 of FIG. 9D. These curves were obtained from an experiment using a polyethylene based film, and d-limonene (106 ppm) as the odorous organic species.

Figure 9C:
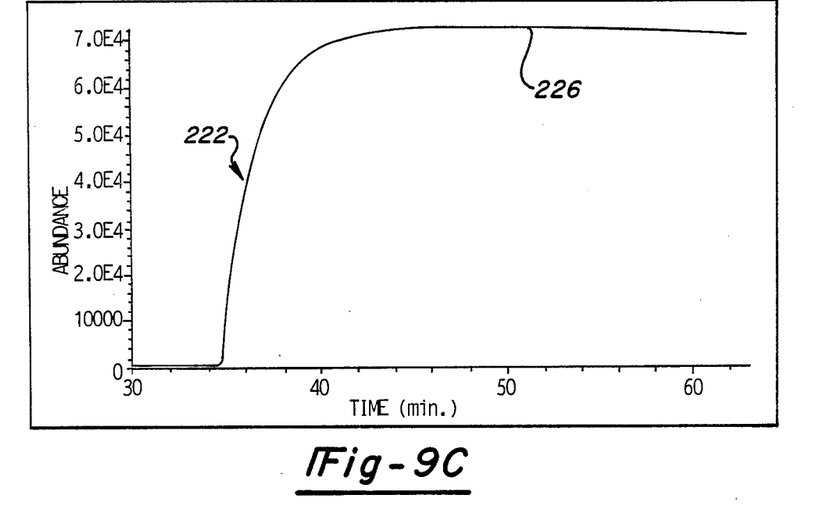
FIG. 9G is an expanded graph of the permeation rate section from the graph shown in FIG. 9A.
FIG. 9D is an expanded graph of the desorption section from the graph shown in FIG. 9A.
Figure 9D:
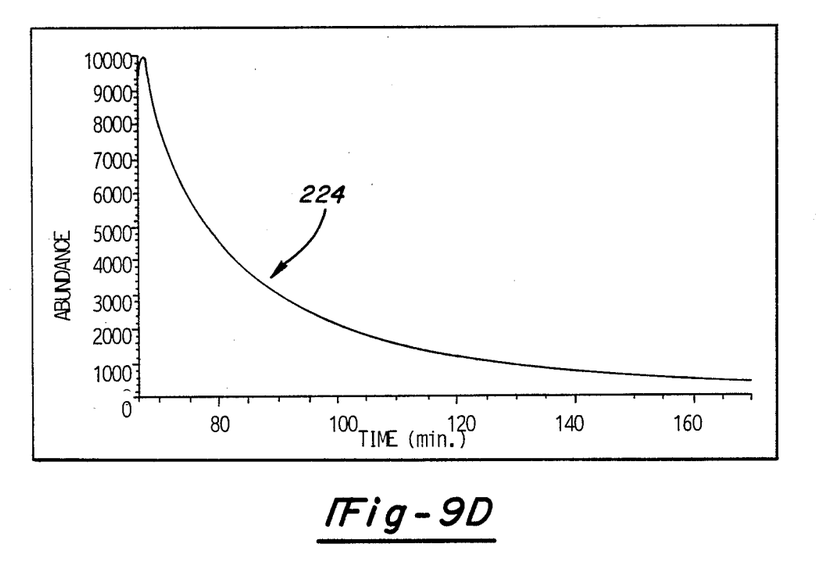

As well known, permeability is a quantity measured at the steady state, such as the curve portion designated by reference numeral 226 in FIGS. 9A and 9C. The transient portion of a permeation curve provides information about diffusivity, which can be evaluated according to two published methods. These methods are described in "Measurement of Hydrogen Isotope Transport in Poly (vinyl flouride) Films by the Permeation-Rate-Method", by K. D. Ziegel, H. K. Frensdorff and D. E. Blair, J. Polym Sci., Part A-2 7 (1969) 809; and "A Dynamic Approach to Diffusion and Permeation Measurements", by R. A. Pasternak, J. F. Schimscheimer and J. Heller, J. Polymer Sci., Part A-2, 8 (1970) 467. These two articles are hereby incorporated by reference.

However, as stated previously, for materials exhibiting fast rising transient permeation rates, the desorption method according to the present invention provides an effective way of determining the diffusivity and solubility coefficients by measuring the actual amount of permeating molecules once the steady state condition has been reached. Once the steady state permeation rate "P" is known, then the diffusivity coefficient "D" and solubility coefficient "S" may be found according to the equation: $P = D \times S$. In this regard, it has been found that the following equation may be used to curve fit the data from the desorption experiment:

$$I = \sum_{i=1}^{3} a_i e^{-b_i t}$$

where I is the mass spectrometric response of an ion at time "t" minutes, with $a_i$ and $b_i$ being the curve fitting parameters. The missing data from the first five minutes between the permeation and desorption experiments may be obtained by the extrapolation of the fitted curve. The total amount of the permeating molecules "W" desorbed from the film may also be evaluated from the following equation:

$$W = C \int_0^\infty \sum_{i=1}^{3} a_i e^{-b_i t} dt$$

$$W = C \sum_{i=1}^{3} a_i / b_i$$

where C is a proportional constant determined from the instrumental sensitivity calibration.

It will be appreciated that the above disclosed embodiment is well calculated to achieve the aforementioned objects of the present invention. In addition, it is evident that those skilled in the art, once given the benefit of the foregoing disclosure, may now make modifications of the specific embodiment described herein without departing from the spirit of the present invention. Such modifications are to be considered within the scope of the present invention which is limited solely by the scope and spirit of the appended claims.

What is claimed:

1. A system for measuring the permeation rate of organic molecules across a polymer film, comprising:
   chamber means for supporting a polymer film sample and permitting an upstream side of said polymer film sample to be swept with a fluid containing organic molecules and a downstream side of said polymer film sample to be swept with a carrier fluid under substantially atmospheric pressure and controlled environmental conditions on at least the upstream side of said polymer film sample;
   interface means in communication with the downstream side of said polymer film sample for enabling organic molecules which have permeated across said polymer film sample to be subjected to low pressure mass spectrometry analysis; and
   mass spectrometer means for analyzing the concentration of said permeant organic molecules in said carrier gas.

2. The system according to claim 1, wherein said chamber means includes permeation cell means for supporting said polymer film sample within said chamber means, said cell means providing a cavity on both the upstream and downstream sides of said polymer film sample, and entry and exit port means for permitting separate fluid flow through both said upstream and downstream cavities.

3. The system according to claim 2, wherein said chamber means includes oven means for controlling the temperature within said chamber means.

4. The system according to claim 3, wherein said chamber means includes humidifier mean for controlling the humidity in at least said upstream cavity of said cell means.

5. The system according to claim 2, wherein said chamber means includes fluid handling means for alternatively supplying a calibration fluid and said organic molecule containing carrier fluid to said interface means.

6. The system according to claim 1, wherein said interface means is a flow-through hollow fiber probe.

7. An apparatus for permitting one side of a polymer film sample to be exposed to a fluid containing molecules for testing the permeation of said molecules through said polymer film sample, comprising:
   a permeation cell; and
   means for holding said polymer film sample in a predetermined position before and after insertion into said permeation cell;
   said permeation cell having
   a pair of rigid members for supporting said holding means within said permeation cell, said rigid members being formed to provide an upstream cavity and a downstream cavity across said polymer film sample, said upstream cavity having first entry and exit port means for enabling said molecule containing fluid to be conveyed into and out of said upstream cavity, and said downstream cavity having second entry and exit port means for enabling permeant organic molecules in said downstream cavity to be conveyed from said downstream cavity by a carrier fluid for analysis, and
   pneumatic means for moving said pair of rigid members into and out of a sealing engagement with said holding means.

8. The apparatus according to claim 7, wherein said holding means comprises at least one card having adhesive means on one side thereof for mounting said polymer film sample to said card, and aperture means for exposing said polymer film sample to both said upstream and downstream cavities of said permeation cell.

9. The apparatus according to claim 8, wherein said holding means includes a pair of said cards, such that said polymer film membrane is interposed between said cards.

10. The apparatus according to claim 7, wherein each of said rigid members comprise a metal disk, one of said metal disk being an upstream disk and the other of said disks being a downstream disk.

11. The apparatus according to claim 10, wherein one of said disks has elastomeric means for providing a seal around the cavity of said disk.

12. The apparatus according to claim 7, wherein said moving means includes cylinder means for moving said rigid members into and out of engagement under fluid pressure.

13. The apparatus according to claim 12, wherein said moving means further includes a pair of stationary end plates, and said cylinder means includes a pair of fluid pressure actuated cylinders, each of said cylinders being interposed between one of said end plates and one of said rigid members.

14. The apparatus according to claim 13, wherein said end plates form part of a housing for said permeation cell, and said housing includes a top section having a slot formed therein for permitting said holding means to be inserted into and extracted from said permeation cell.

15. The apparatus according to claim 14, wherein each of said cylinders comprises a pneumatic cylinder.

16. A method of measuring the permeability of a film using mass spectrometry analysis, comprising the steps of:
   placing said film into a permeation chamber having an upstream side and a downstream side;
   calibrating a mass spectrometer using a first predetermined concentration of a vapor containing permeant molecules;
   causing a second predetermined concentration of permeant molecules to enter said upstream side of said permeation chamber and measuring the permeation rate across said film from the downstream side of said permeation chamber;
   removing residual permeant molecules from said upstream side of said permeation chamber; and
   measuring the desorption of said permeant molecules from said film by mass spectrometry.

* * * * *

UNITED STATES PATENT AND TRADEMARK OFFICE
CERTIFICATE OF CORRECTION

PATENT NO. : 4,944,180

DATED : July 31, 1990

INVENTOR(S) : James C. Tou and Donald C. Rulf

It is certified that error appears in the above-identified patent and that said Letters Patent is hereby corrected as shown below:

Column 2, line 34 "stresses." should correctly read --stresses,--.

Column 3, line 45 "9G" should correctly read --9C--.

Column 4, line 57 "ZS Ia" should correctly read --28 is--.

Column 7, line 11 "110.112" should correctly read --110-112--.

Column 8, line 22 "174.178" should correctly read --174-178--.

Column 9, line 9 "valve G" should correctly read --valve C--.

Signed and Sealed this

Seventh Day of January, 1992

Attest:

HARRY F. MANBECK, JR.

*Attesting Officer*   *Commissioner of Patents and Trademarks*